United States Patent [19]
Chao

[11] Patent Number: 5,631,716
[45] Date of Patent: May 20, 1997

[54] SPORTS GOGGLES HAVING PRESCRIPTION LENS

[76] Inventor: David Y. Chao, 1120 Green Acre Rd., Towson, Md. 21204

[21] Appl. No.: 670,606

[22] Filed: Jun. 26, 1996

[51] Int. Cl.⁶ .................................. G02C 5/00; A61F 9/02
[52] U.S. Cl. .................................. 351/41; 351/154; 2/426
[58] Field of Search .................................. 351/41, 83, 86, 351/96, 103–106, 154, 178; 2/426, 431, 440, 443

[56] References Cited

U.S. PATENT DOCUMENTS 5,387,950  2/1995  Weltmann .................................. 351/154

Primary Examiner—Huy Mai
Attorney, Agent, or Firm—Charles E. Baxley, Esq.

[57] ABSTRACT

A pair of goggles includes two shields each having an opening and a peripheral recess formed in the center portion for receiving a pair of rings and prescription lenses. The shields each includes a front peripheral flange and a rear peripheral flange for defining the peripheral recess. The rear peripheral flange includes a height greater than that of the front peripheral flange so as to prevent the prescription lens from moving beyond the peripheral flange. The side portions of the shields will not be occluded by the prescription lenses.

2 Claims, 3 Drawing Sheets

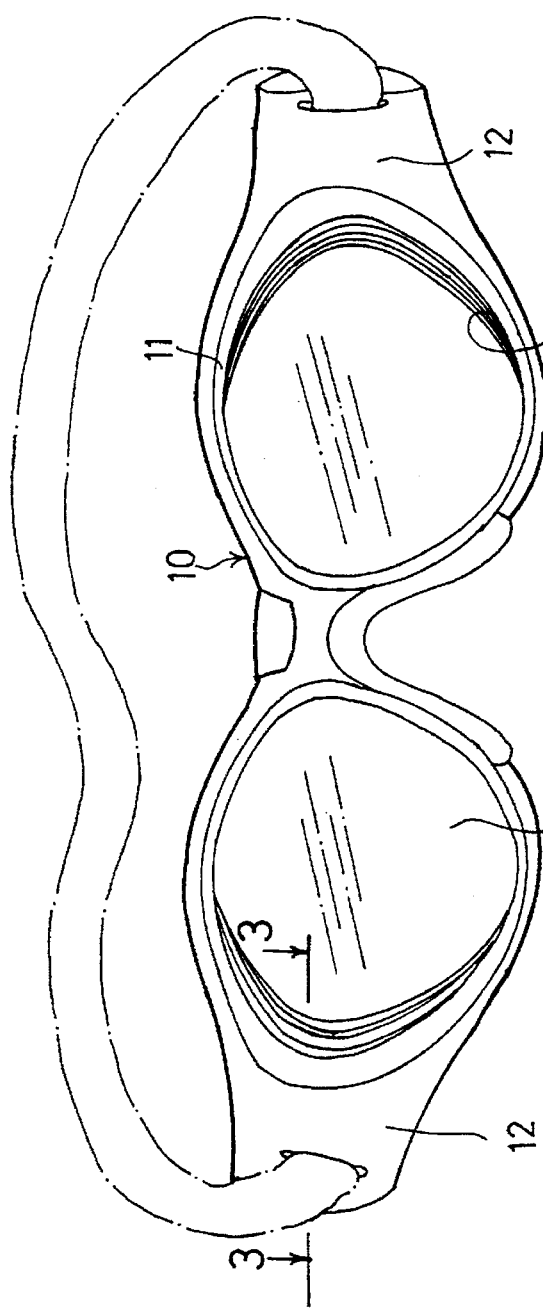
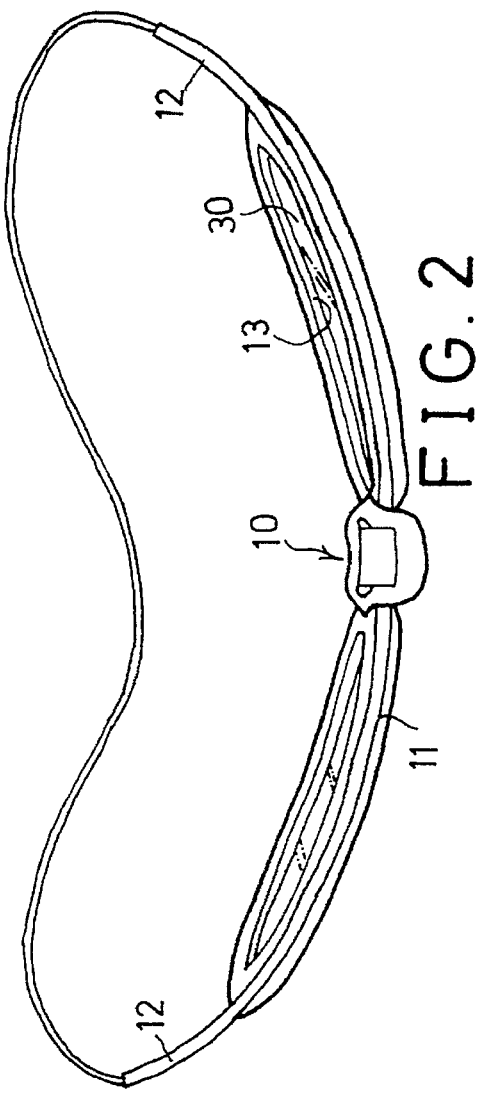
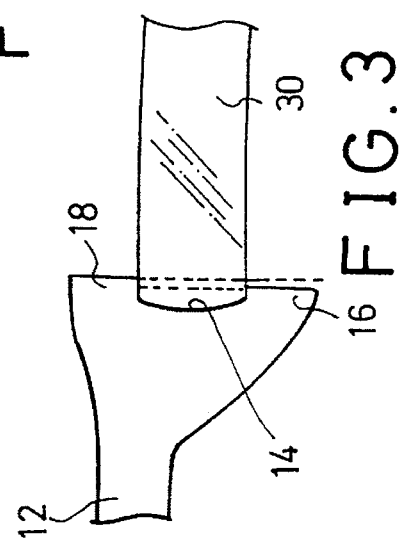

SPORTS GOGGLES HAVING PRESCRIPTION LENS

BACKGROUND OF THE INVENTION

1. Field of the Invention

The present invention relates to a goggle frame, and more particularly to a pair of sports goggles having a pair of prescription lenses.

2. Description of the Prior Art

Typical sports goggles comprise a frame body for securing lenses therein. However, the lenses are not prescription lenses such that an auxiliary frame is required to be attached to the sports goggles for carrying prescription lenses. U.S. Pat. No. 5,412,438 to Bolle, U.S. Pat. No. 5,428,407 to Sheffield and U.S. Pat. No. 5,493,348 to Herald Jr., disclose three typical mechanisms for attaching the auxiliary frame to the sports goggles or to the safety glasses. However, the most important requirement for the sports goggles is that the lenses will not hurt the eyes of the user. However, the auxiliary frame and the auxiliary lenses engaged in the auxiliary frame will hurt the user when a ball hits onto the sports goggles or the safety glasses from the front portion thereof. In addition, it is very important that the side portions of the sports goggles are not shielded or occluded such that the user may clearly see the side portions. However, the auxiliary frame may occlude the side portions.

U.S. Pat. No. 5,387,950 to Weltmann discloses a pair of prescription lenses that are permanently affixed within the apertures of the lens shield and that may not be easily replaced with a brand new one.

U.S. Pat. No. 4,021,103 to Gaspari discloses an ophthalmic mounting arrangement which includes a pair of lens liners that may be engaged in a spectacle frame having a hollow cavity that should be formed in the bridge area. In addition, the lens liners are engaged in the frames and may not be used for engaging in the lens shields directly. Furthermore, the ophthalmic mounting arrangement may not be used in sports goggle which includes a pair of lenses that may not be moved beyond the spectacle frame in order to be prevented from hurting the user.

The present invention has arisen to mitigate and/or obviate the afore-described disadvantages of the conventional sports goggles.

SUMMARY OF THE INVENTION

The primary objective of the present invention is to provide a pair of sports goggles which includes two prescription lenses secured therein without occluding the side portions of the sports goggles.

The other objective of the present invention is to provide a pair of sports goggles which includes two prescription lenses that may be easily replaced with a brand new one.

In accordance with one aspect of the invention, there is provided a pair of goggles comprising a frame body including two shields provided therein, the shields each including an outer side portion and each including an opening formed therein, a pair of rings for engaging with the openings of the shields and each including an outer peripheral recess for engaging with a peripheral wall defining the opening and each including an outer rear peripheral flange and an outer front peripheral flange for defining the outer peripheral recess, the rings each including an inner peripheral recess and each including an inner rear peripheral flange and an inner front peripheral flange for defining the inner peripheral recess, and a pair of prescription lenses engaged in the inner peripheral recesses of the rings and engaged with the inner front and the inner rear peripheral flanges. The outer front peripheral flange of the ring includes a height greater than that of the outer rear peripheral flange so as to prevent the ring from moving beyond the shields. The inner rear peripheral flange of the ring includes a height greater than that of the inner front peripheral flange so as to prevent the prescription lens from moving beyond the inner rear peripheral flange.

Further objectives and advantages of the present invention will become apparent from a careful reading of a detailed description provided hereinbelow, with appropriate reference to accompanying drawings.

BRIEF DESCRIPTION OF THE DRAWINGS

FIG. 1 is a front view of a pair of sports goggles in accordance with the present invention;

FIG. 2 is a top view of the sports goggles;

FIG. 3 is a cross sectional view taken along lines 3—3 of FIG. 1;

DETAILED DESCRIPTION OF THE PREFERRED EMBODIMENT

Figure 4:
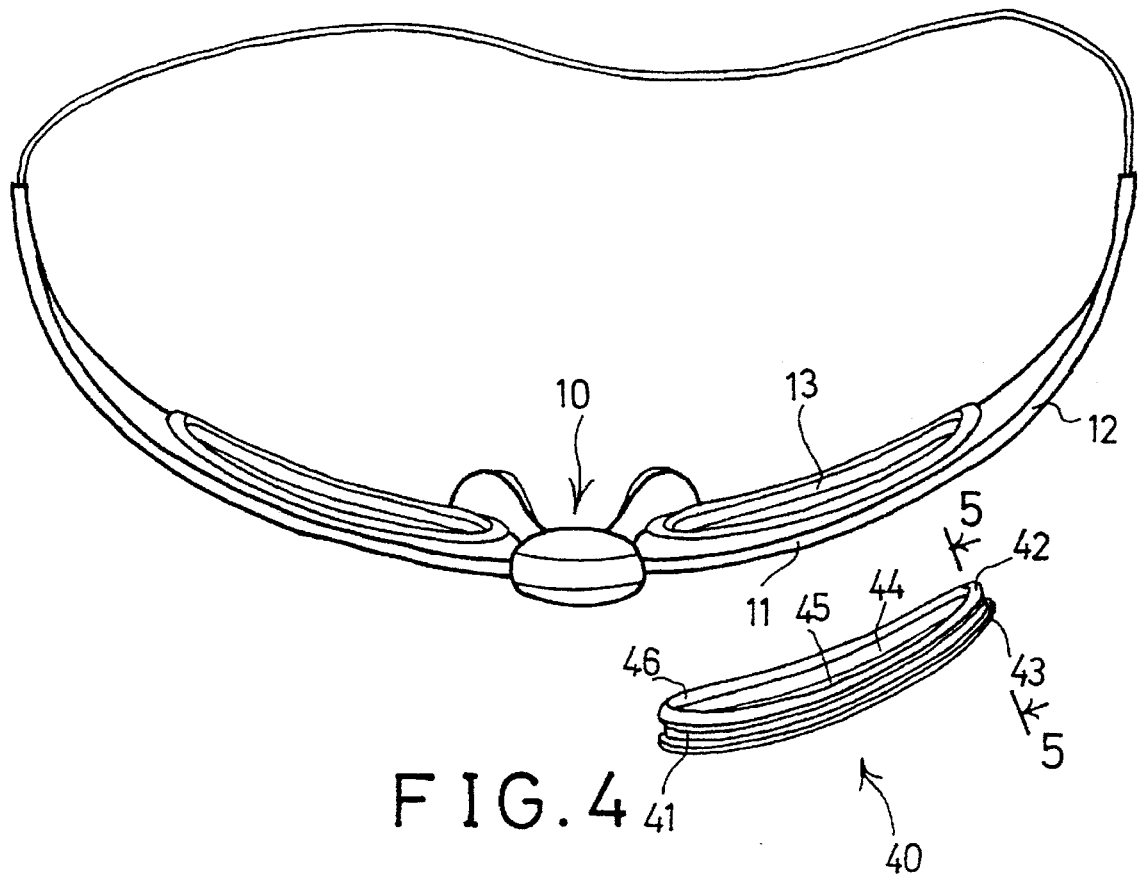
FIG. 4 is a partial exploded view illustrating an application of the sports goggles.

Referring to the drawings, and initially to FIGS. 1 to, a pair of sports goggles in accordance with the present invention comprises a rimless frame body 10 having two shields 11 provided therein and having a resilient belt 20 engaged to the side portions for securing the frame body 10 to the head of a user. The shields 11 of the frame body 10 are preferably made of poly carbonate material and are formed integral by molding process such that the frame body 10 can be bent without being damaged and such that the frame body 10 will not hurt the user when hit by a ball. It is very important that the side portions 12 of the shields 11 of the sports goggles are not shielded or occluded such that the user may clearly see the side portions. The shields 11 each includes an opening 13 formed therein and a peripheral recess 14 formed therein for engaging with a prescription lens 30 therein and each includes a front peripheral flange 16 and a rear peripheral flange 18 for defining the peripheral recess 14 therebetween. The rear peripheral flange 18 includes a height greater than that of the front peripheral flange 16 such that the contact area between the rear peripheral flange 18 and the prescription lens 30 is greater than that between the front peripheral flange 16 and the prescription lens 30, and such that the prescription lens 30 can be prevented from moving beyond the peripheral flange 18. The eyes of the user may thus be protected and prevented from being hurt by the prescription lens 30. The shorter front peripheral flange 16 allows the prescription lens 30 to be engaged into the peripheral recess 14.

It is to be noted that the prescription lenses 30 are arranged such that the side portions 12 of the frame body 10 will not be occluded by the prescription lenses 30, best shown in FIG. 3.

Figure 5:
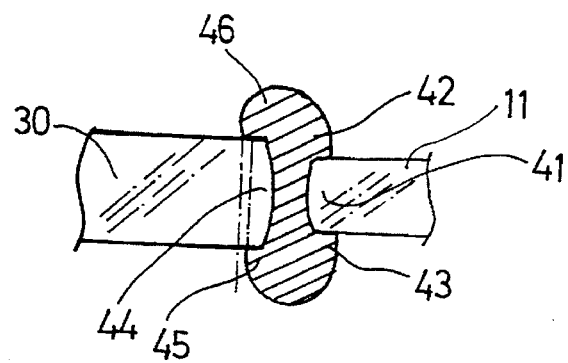
FIG. 5 is a cross sectional view taken along lines 5—5 of FIG. 4.

As shown in FIGS. 4 and 5, alternatively, no peripheral recess is formed in the opening 13. Instead, a ring 40 is engaged in the opening 13 and includes an outer peripheral recess 41 for engaging with the peripheral wall defining the opening 13. The outer peripheral recess 44 is formed and defined between a lower rear peripheral flange 42 and a higher front peripheral flange 43. The lower rear peripheral flange 42 may allow the ring 40 to be easily engaged into the opening 13 and the higher front peripheral flange 43 may prevent the ring 40 from moving inward toward the user and beyond the lens 11. The ring 40 includes an inner peripheral recess 44 for engaging with the prescription lens 30 (FIG. 5). The inner peripheral recess 44 is formed and defined between a lower front peripheral flange 45 and a higher rear peripheral flange 46. The lower front peripheral flange 45 may allow the prescription lens 30 to be engaged into the ring 40 and the higher rear peripheral flange 46 may prevent the prescription lens 30 from moving inward toward the user and beyond the lens 11.

Figure 6:
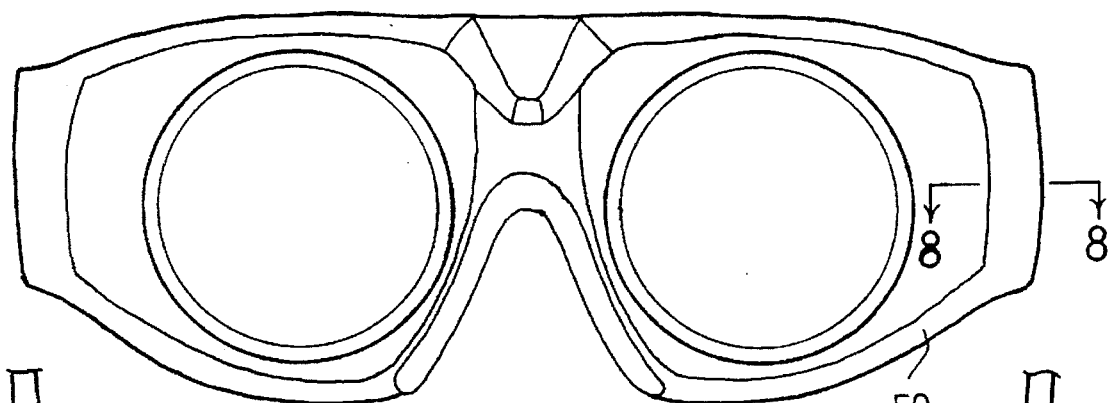
FIG. 6 is a front view illustrating another application of the sports goggles.
Figure 7:
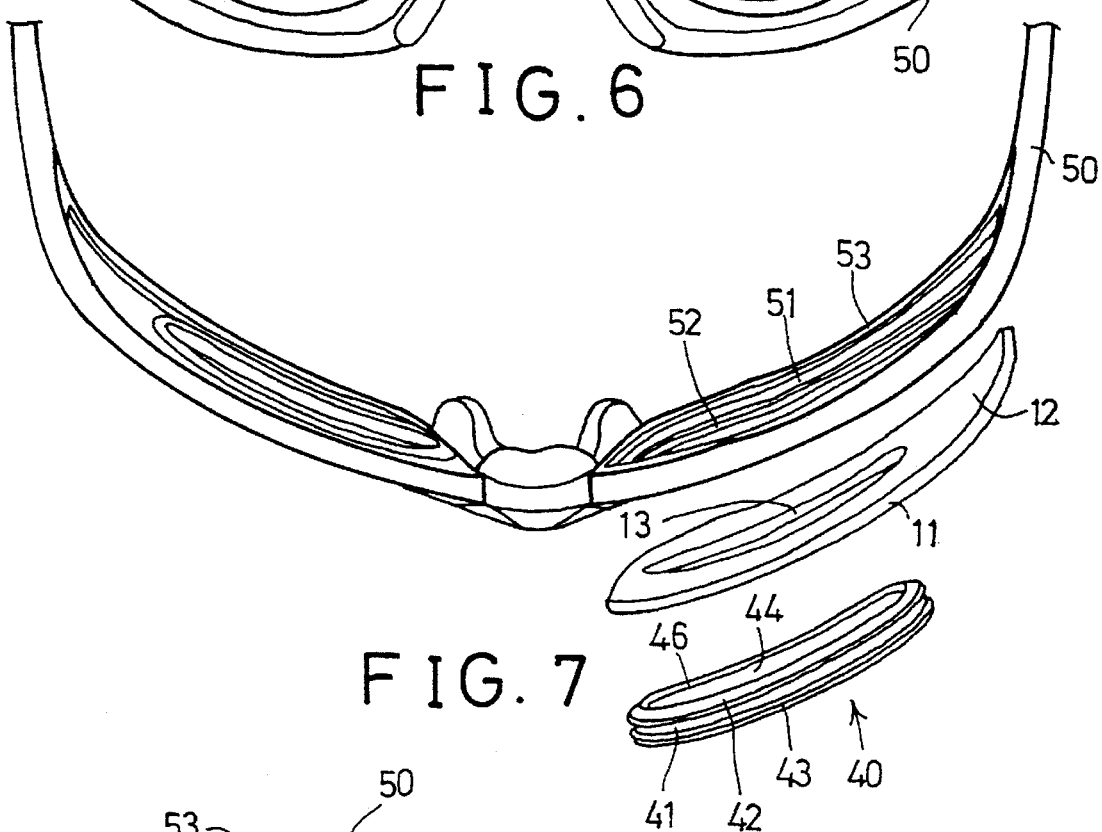
FIG. 7 is a partial exploded view illustrating the sports goggles as shown in FIG. 6.
Figure 8:
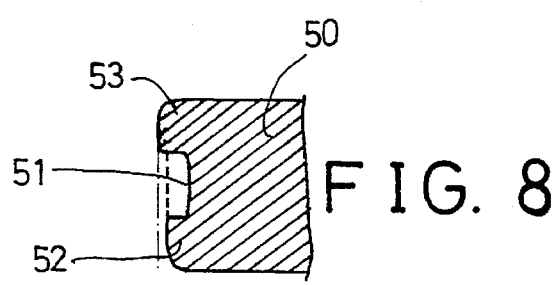
FIG. 8 is a cross sectional view taken along lines 8—8 of FIG. 6.

As shown in FIGS. 6 to 8, the sports goggles may include an outer frame 50 having two inner peripheral recesses 51 formed therein for engaging with the shields 11. The shields 11 each also includes an opening 13 formed therein for engaging with prescription lenses 30 therein. The inner peripheral recesses 51 each is formed and defined between a lower front peripheral flange 52 and a higher rear peripheral flange 53. The lower front peripheral flange 52 may allow the prescription lens 30 to be engaged into the ring 40 and the higher rear peripheral flange 53 may prevent the prescription lens 30 from moving inward toward the user and beyond the lens 11.

The typical safety glasses are provided for bicycle riders and include a rimless lower portion and a bar provided on top of the glasses or shields. The shields also include a large size having two side portions that may not be shielded or occluded. The shields may also include two openings formed therein for engaging with the prescription lenses therein such that the prescription lenses will not occlude the side portions of the shields.

Accordingly, the sports goggles in accordance with the present invention includes two prescription lenses secured therein without occluding the side portions of the sports goggles. The prescription lenses may be easily replaced with a brand new one.

Although this invention has been described with a certain degree of particularity, it is to be understood that the present disclosure has been made by way of example only and that numerous changes in the detailed construction and the combination and arrangement of parts may be restored to without departing from the spirit and scope of the invention as hereinafter claimed.

I claim:

1. A pair of goggles, comprising:

a frame body including two shields provided therein, said shields each including an outer side portion and each including an opening formed therein and defined by a peripheral wall, a pair of rings for engaging with said openings of said shields and each including an outer peripheral recess for engaging with said peripheral wall of said opening and each including an outer rear peripheral flange and an outer front peripheral flange for defining said outer peripheral recess, said rings each including an inner peripheral recess and each including an inner rear peripheral flange and an inner front peripheral flange for defining said inner peripheral recess, and a pair of prescription lenses engaged in said inner peripheral recesses of said rings and engaged with said inner front and said inner rear peripheral flanges, said outer front peripheral flange of said ring including a height greater than that of said outer rear peripheral flange so as to prevent said ring from moving beyond said shields; and said inner rear peripheral flange of said ring including a height greater than that of said inner front peripheral flange so as to prevent said prescription lens from moving beyond said inner rear peripheral flange.

2. A pair of goggles according to claim 1 further comprising an outer frame including two inner peripheral recesses formed therein for engaging with said shields respectively, said outer frame including two inner peripheral flanges and two outer peripheral flanges for defining said inner peripheral recesses respectively, said inner peripheral flange of said outer frame including a height greater than that of said outer peripheral flange of said outer frame so as to prevent said shield from moving beyond said inner peripheral flange of said outer frame.

* * * * *